United States Patent [19]

Ungemach et al.

[11] Patent Number: 5,202,270

[45] Date of Patent: Apr. 13, 1993

[54] COCAINE AND COCAINE METABOLITES ASSAY TRACERS, IMMUNOGENS AND ANTIBODIES

[75] Inventors: Frank S. Ungemach, Lake Villa; Daniel S. Nam, Chicago, both of Ill.; Oliver H. Meek, Flower Mound, Tex.

[73] Assignee: Abbott Laboratories, Abbott Park, Ill.

[21] Appl. No.: 576,085

[22] Filed: Aug. 30, 1990

Related U.S. Application Data

[63] Continuation of Ser. No. 372,206, Jun. 26, 1989, abandoned, which is a continuation of Ser. No. 284,829, Dec. 13, 1988, abandoned, which is a continuation of Ser. No. 863,671, May 15, 1986, abandoned.

[51] Int. Cl.$^5$ ............... G01N 33/533; C07D 451/02; C07K 13/00
[52] U.S. Cl. .................. 436/537; 436/546; 436/547; 436/805; 436/816; 436/825; 530/389.8; 530/405; 546/126; 546/129; 546/130
[58] Field of Search ............... 436/517, 537, 546, 547, 436/800, 805, 816, 825; 546/126, 128, 129, 130, 132; 530/389.8, 405

[56] References Cited

U.S. PATENT DOCUMENTS

| | | | |
|---|---|---|---|
| 3,888,866 | 6/1975 | Leute et al. | 546/127 |
| 3,917,582 | 11/1975 | Soffer et al. | 435/7 |
| 3,951,748 | 4/1976 | Devlin | 424/87 |
| 3,975,237 | 8/1976 | Rubenstein et al. | 435/7 |
| 4,022,878 | 5/1977 | Gross | 436/804 |
| 4,045,420 | 8/1977 | Soffer et al. | 530/807 |
| 4,123,431 | 10/1978 | Soffer et al. | 436/803 |
| 4,197,237 | 4/1980 | Leute et al. | 436/547 |
| 4,207,307 | 6/1980 | Kaul et al. | 436/518 |
| 4,235,864 | 11/1980 | Kaul et al. | 436/543 |
| 4,255,329 | 3/1981 | Ullman | 436/546 |
| 4,407,965 | 10/1983 | Yanaihara | 424/85 |
| 4,420,568 | 12/1983 | Wang et al. | 436/536 |
| 4,510,251 | 4/1985 | Kirkemo et al. | 436/536 |
| 4,668,640 | 5/1987 | Wang et al. | 436/536 |

FOREIGN PATENT DOCUMENTS 2601141 7/1986 France.

OTHER PUBLICATIONS

Colbert Ann Clin Biochem 1986 23, 37–41.
Hackh's Chemical Dictionary, Third Edition, McGraw-Hill Book Co., N.Y., p. 43 (1944).
Jatlow, Peter I., et al., "Measurement of Benzoylecgonine and Cocaine in Urine, Separation of Various Cocaine Metabolites Using Reversed-Phase High-Performance Liquid Chromatography," Journal of Chromatography, 152:115–121 (1978).

*Primary Examiner*—Mary E. Ceperley
*Attorney, Agent, or Firm*—Thomas M. Breininger; Lawrence S. Pope

[57] ABSTRACT

The present invention is directed to a fluorescence polarization assay for benzoyl ecgonine and substituted benzoyl ecgonine compounds in biological fluids, and to a method of making reagents therefor. Specifically, tracers, immunogens and antibodies are disclosed. The tracers and the immunogens are made from substituted benzoyl ecgonine compounds. A fluorescein moiety is included in the tracer, while a poly(amino acid) forms a part of the immunogen. The assay is conducted by measuring the degree of polarization retention of plane polarized light that has been passed through a sample containing antiserum and tracer.

16 Claims, 4 Drawing Sheets

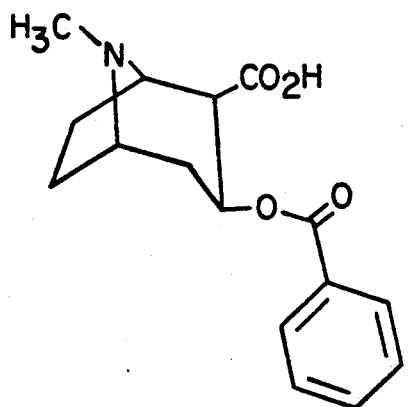
FIG.1
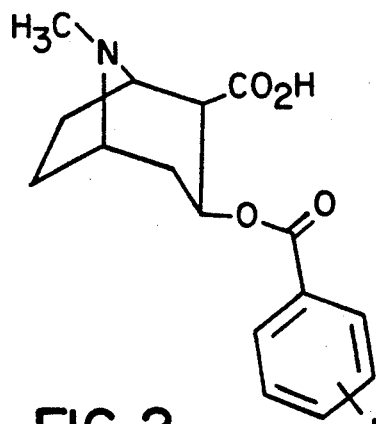
FIG.2
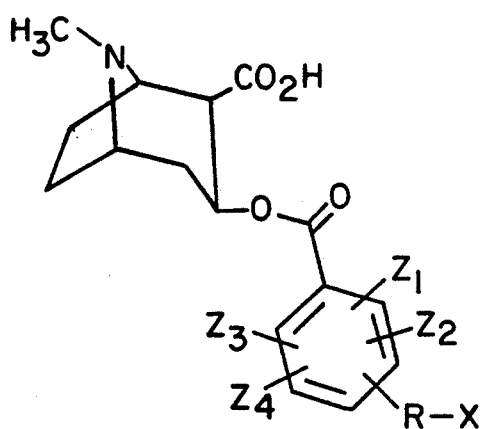
FIG.3
FIG.4
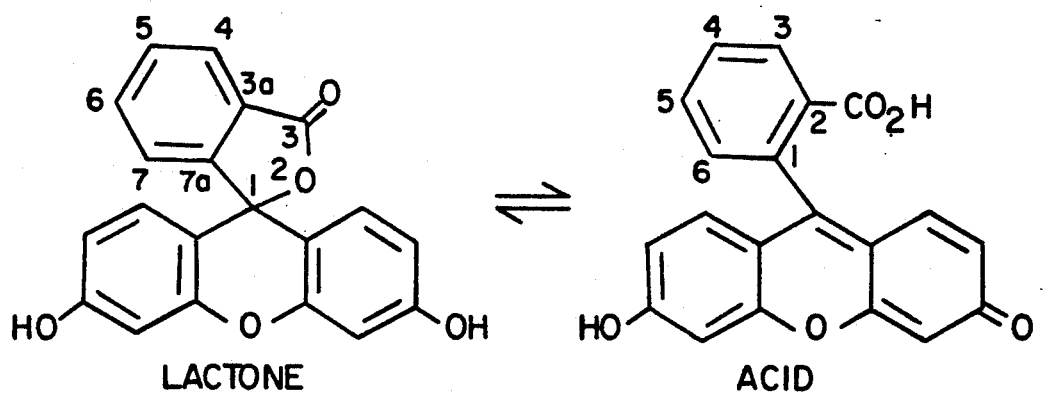
LACTONE ⇌ ACID

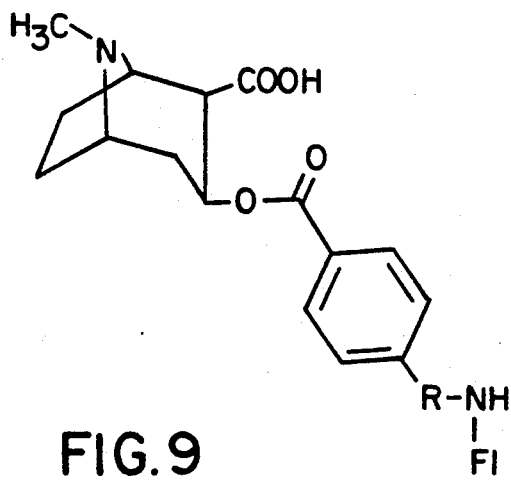
FIG.9
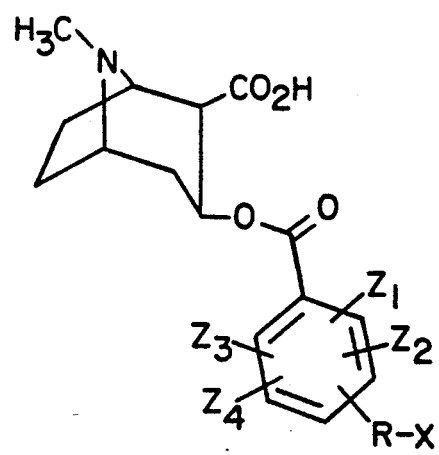
FIG.10
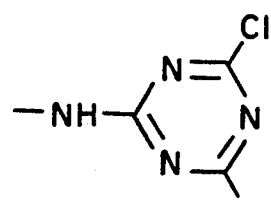
FIG.11-1
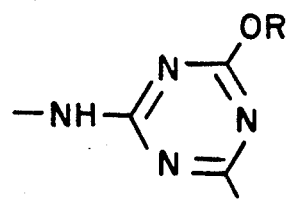
FIG.11-2
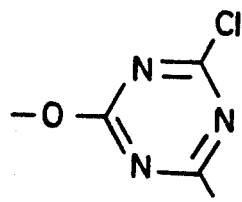
FIG.11-3
—CO—
FIG.11-4
—CNH—
FIG.11-5
—NH—CO—
FIG.11-6
—NH—CS—
FIG.11-7

EXAMPLE VIII

COCAINE AND COCAINE METABOLITES ASSAY TRACERS, IMMUNOGENS AND ANTIBODIES

This application is a continuation of application Ser. No. 372,206, filed Jun. 26, 1989, now abandoned, which is a continuation of application Ser. No. 284,829, filed Dec. 13, 1988, now abandoned, which is a continuation of application Ser. No. 863,671, filed May 15, 1986, now abandoned.

BACKGROUND OF THE INVENTION

1. Technical Field

The presence invention relates to a method and reagents for a fluorescence polarization immunoassay procedure for determining the presence or amount of benzoyl ecgonine and substituted benzoyl ecgonine compounds in fluids, especially biological fluids such as urine, serum or plasma, and to a method of making the reagents. More specifically, the invention relates to (1) reagents (tracers and antibodies) for determining the presence or amount of benzoyl ecgonine and substituted benzoyl ecgonine compounds in a sample; (2) immunogen compounds used to raise antibodies; (3) synthetic methods (for making tracers and immunogen compounds); and (4) analytical methods for conducting the assay.

2. Background Art

Cocaine is a very potent central nervous system stimulant. It is a naturally occurring alkaloid found in the leaves of the shrub species Erythroxylon and Erythroxylaceae. It historically has been used as a local anesthetic, but due to its stimulant properties, abuse has lead to increasing efforts to police its use and prevent its unauthorized distribution. These efforts are supported by detection methods that are rapid, reliable and selective for cocaine and/or cocaine metabolites. Cocaine is not highly toxic but is addictive. Cocaine is rapidly metabolized. In blood and urine the two major metabolites are benzoyl acgonine and ecgonine methyl ester, neither of which is pharmacologically active. Detection of either or both of these metabolites indicates cocaine use.

The most frequent biological fluid tested is urine. Urine samples are more accessible than blood samples, and other biological fluids have not been extensively investigated for use in assays.

In the past, urine samples have been tested for the presence of cocaine and cocaine metabolite by thin layer chromatography, enzyme immunoassay, gas chromatography or high performance liquid chromatography (HPLC) assays. These methods are not without drawbacks; for example, the assay time can typically be lengthy.

In assays for other substances, competitive binding immunoassays have provided a more satisfactory alternative. Typically, competitive binding immunoassays are used for measuring ligands in a test sample. (For the purposes of this disclosure, a "ligand" is a substance of biological interest to be quantitatively determined by a competitive binding immunoassay technique.) The ligands compete with a labeled reagent, or "ligand analog" or "tracer" for a limited number of receptor binding sites on antibodies specific to the ligand and ligand analog. The concentration of a ligand in the sample determines the amount of ligand analog which binds to the antibody; the amount of ligand analog that will bind is inversely proportional to the concentration of ligand in the sample, because the ligand and the ligand analog each bind to the antibody in proportion to their respective concentrations.

Fluorescence polarization provides a quantitative means for measuring the amount of tracer-antibody conjugate produced in a competitive binding immunoassay. Fluorescence polarization techniques are based on the principle that a fluorescent labeled compound, when excited by plane polarized light, will emit fluorescence having a degree of polarization inversely related to its rate of rotation. Accordingly, when a tracer-antibody conjugate having fluorescent label is excited with plane polarized light, the emitted light remains highly polarized because the fluorophore is constrained from rotating between the time that light is absorbed and emitted. In contrast, when an unbound tracer is excited by plane polarized light, its rotation is much faster than the corresponding tracer-antibody conjugate and the molecules are more randomly oriented. As a result, the light emitted from the unbound tracer molecules is depolarized.

A problem that heretofore has prevented the accurate determination of cocaine and other "drugs of abuse" in urine by fluorescence polarization techniques is that of riboflavin interference. Riboflavin, or vitamin $B_2$, is a common constituent of many foods and of commercially available vitamin supplements. Riboflavin is excreted primarily in the urine and has a fluorescence spectrum quite similar to that of fluorescein. As as result, the presence of riboflavin in even moderate amounts in urine samples creates an interference which can produce erroneous data. While ordinary consumption of riboflavin is unlikely to produce more than trace amounts of riboflavin in the urine, test results can readily be distorted by the consumption of excessive quantities of vitamin supplements by persons wishing to prevent detection of cocaine use.

The present invention offers an advance in the art in that highly sensitive tracers, a method for making the tracers, and an assay using the tracers are provided specifically for the determination of benzoyl ecgonine and substituted benzoyl ecgonine compounds without riboflavin interference.

SUMMARY OF THE INVENTION

The present invention is directed to a fluorescence polarization assay for benzoyl ecgonine and substituted benzoyl ecgonine compounds; to tracers, immunogens and antibodies for use in the assay; and to methods for making the tracers, immunogens and antibodies.

A first aspect of the invention relates to the discovery of unique tracers and immunogens having novel structures. According to the first aspect of the invention, the tracers and the immunogens can both be represented by the structural formula shown in FIG. 5 where:

Q is a poly(amino acid), a poly(amino acid) derivative, fluorescein, or a fluorescein derivative other than carboxyfluorescein;

X is NH where Q is a poly(amino acid) or a poly(amino acid) derivative; and X is NH or CO when Q is fluorescein or a fluorescein derivative other than carboxyfluorescein;

R is a linking group including up to 2 heteroatoms when Q is a poly(amino acid) or a poly(amino acid) derivative and up to 4 heteroatoms when Q is fluorescein or a fluorescein derivative, and having a total of from 1 to 8 carbon atoms and heteroatoms; and $Z_1$, $Z_2$, $Z_3$, and $Z_4$ are each independently H or F when Q is fluorescein or a fluorescein derivative, and are each H when Q is a poly(amino acid) or a poly(amino acid) derivative.

When Q is a poly(amino acid) or a derivative thereof the compound can be used as an immunogen. When Q is fluorescein or a derivative thereof, the compound can be used as a tracer.

A second aspect of the invention relates to antibodies raised by the novel immunogen. According to the second aspect of the invention, antibodies are prepared in response to a compound according to claim 1 when Q is a poly(amino acid) or a derivative thereof.

According to a third aspect of the invention, an immunogen is made by a method comprising the step of coupling a compound represented by the structural formula shown in FIG. 2, where R is a linking group including up to 2 heteroatoms and having a total of from 1 to 8 carbon atoms and heteroatoms with a poly(amino acid) or a derivative of a poly(amino acid).

According to a fourth aspect of the invention, a method is provided for making a tracer by coupling a compound represented by the structural formula shown in FIG. 3, where:

X is $NH_2$, COOH or CN;

R is a linking group including up to 4 heteroatoms and having a total of from 1 to 8 carbon atoms and heteroatoms; and $Z_1$, $Z_2$, $Z_3$, and $Z_4$ are each independently H or F; with fluorescein or a derivative of fluorescein.

A fifth aspect of the invention relates to the elimination of potential fluorescence interference by riboflavin. Riboflavin binding protein (RBP) is added either directly to each sample or to one or more of the reagents utilized in the assay, wherein it binds all riboflavin present into RBP-riboflavin complexes, thus eliminating fluorescence interference.

According to a sixth aspect of the invention, a process for detecting or measuring the concentration of benzoyl ecgonine and substituted benzoyl ecgonine compounds is provided. A sample is contacted with a benzoyl ecgonine anti-serum, and a fluorescein-containing benzoyl-ecgonine derivative capable of producing a detectable fluorescence polarization response to the presence of the benzoyl ecgonine antiserum. Plane-polarized light is then passed through the solution to obtain a fluorescence polarization response, and this response is detected as a measure of the amount of benzoyl ecgonine and substituted benzoyl ecgonine compounds in the sample.

Further objects and attendant advantages of the invention will be best understood from a reading of the following detailed description taken together with the drawings of the Examples.

BRIEF DESCRIPTION OF THE DRAWINGS

In the following Figures the symbol "Fl" represents fluorescein or a fluorescein derivative and the various other symbols are noted in the Detailed Description.

FIG. 1 shows the general structure of the class of benzoyl ecgonine compounds to be quantitatively or qualitatively determined in accordance with the present invention.

FIG. 2 shows a class of reactants for a method of making an immunogen in accordance with the present invention.

FIG. 3 shows a class of reactants for a method of making a tracer in accordance with the present invention.

FIG. 4 shows the alternate structural formulae and names of the fluorescein moiety included in the tracers of the present invention.

FIG. 9 shows a structural formula for preferred tracers of the present invention.

FIG. 10 shows a precursor for the immunogens shown in FIGS. 6 and 8 and for the tracers shown in FIGS. 7 and 9.

FIG. 11 shows various linkages that couple the fluorescein moiety to the precursor at the X position in FIG. 10, when FIG. 10 represents a precursor for the tracers shown in FIGS. 7 and 9. The partially-unattached single bond at the left end of each of the linkage molecules represents the position at which the linkage molecule attaches to the precursor and the partially-unattached single bond at the right end of each of the linkage molecules represents the position at which the linkage molecule attaches to the fluorescein moiety.

FIGS. 12 and 13 show two examples of structures of tracers in accordance with the present invention.

FIGS. 14 and 15 show two examples of structures of hapten reactants used to form the immunogens of the present invention.

DETAILED DESCRIPTION OF THE PREFERRED EMBODIMENTS

Figure 5:
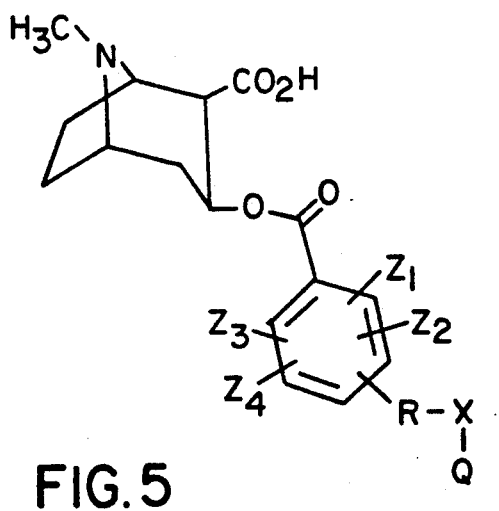
FIG. 5 shows a general structural formula for the tracers and the immunogens of the present invention.

The various aspects of the invention will now be discussed in relation to the Figures and/or the Examples.

The present invention involves the use of fluorescein and derivatives of fluorescein. In particular, a necessary property of fluorescein and its derivatives for the usefulness of the tracer compounds is the fluorescence of fluorescein. Fluorescein exists in two tautomeric forms, illustrated in FIG. 4, depending on the acid concentration (pH) of the environment. In the open (acid form), there are a number of conjugated double bonds which make that form of fluorescein (and compounds containing a fluorescein moiety) capable of absorbing blue light and emitting green fluorescence after an excited state lifetime of about 4 nanoseconds. When the open and closed forms coexist, the relative concentration of molecules in the open and closed forms is easily altered by adjustment of the pH level. Generally, the tracer compounds of the present invention exist in solution as biologically acceptable salts such as sodium potassium, ammonium and the like, which allows the compounds to exist in the open, fluorescent form, when employed in the analytical methods of the present invention. The specific salt present will depend on the buffer employed to adjust the pH level. For example, in the presence of a sodium phosphate buffer, the compounds of the present invention will generally exist in the open form, as a sodium salt.

As used herein, the term "fluorescein," either as an individual compound or as a component of a larger compound, is meant to include both the open and closed forms, if they exist for a particular molecule, except in the context of fluorescence. An open form is necessary for the fluorescence to occur.

The numbering of carbon atoms of the fluorescein molecule varies, depending upon whether the open or closed form of the molecule is considered. Accordingly, the literature concerning fluorescein and its compounds is not uniform as to carbon atom numbering. In the closed form, the para-carbon to the carbonyl of the lactone on the phenyl ring is numbered 6 (this is sometimes denominated "isomer II"). In the open form, the para-carbon to the carboxylic acid group on the phenyl ring is numbered 5 (this is sometimes denominated "isomer I"). FIG. 4 illustrates these isomers. For the purpose of this disclosure the numbering of the closed form is adopted because the raw materials used in the syntheses are most popularly numbered with that system. The carbon atom of fluorescein and its compounds which is opposite the carboxyl group is therefore numbered "6" for the purposes of the present disclosure.

A tracer which is not complexed to an antibody is free to rotate in less than the time required for absorption and re-emission of the fluorescent light. As a result, the re-emitted light is relatively randomly oriented so that the fluorescence polarization of a tracer not complexed to an antibody is low, approaching zero. Upon complexing with a specific antibody, the tracer-antibody complex thus formed assumes the rotation of the antibody molecule which is slower than that of the relatively small tracer molecule, thereby increasing the polarization observed. Therefore, when a ligand competes with the tracer for antibody sites, the observed polarization of fluorescence of the tracer-antibody complex becomes a value somewhere between that of the tracer and tracer-antibody complex. If a sample contains a high concentration of the ligand, the observed polarization value is closer to that of the free tracer, i.e., low. If the test sample contains a low concentration of the ligand, the polarization value is closer to that of the bound tracer, i.e., high. By sequentially exciting the reaction mixture of an immunoassay with vertically and then horizontally polarized light and analyzing only the vertical component of the emitted light, the polarization of fluorescence in the reaction mixture may be accurately determined. The precise relationship between polarization and concentration of the ligand to be determined is established by measuring the polarization values of calibrators with known concentrations. The concentrations of the ligand can be extrapolated from a standard curve prepared in this manner.

The particular tracers formed in accordance with this invention have been found to produce surprisingly good assays, as will be demonstrated later in this disclosure.

The Reagents

Both the immunogens and the tracers of the present invention can be represented by the general structural formula set forth in the Summary of the Invention, and illustrated in FIG. 5. When Q is a poly(amino acid), the structure represents the immunogen; when Q is a fluorescein derivative, the structure represents the tracer.

The objective is to have competition between benzoyl ecgonine, substituted benzoyl ecgonine compounds and the tracer for the recognition sites of the antibody. Great variations in the structure of the haptens and tracers are allowed in achieving this goal. For the purposes of this invention, "haptens" are precursors of the immunogens, comprising generally a substituted benzoyl ecgonine derivative and a linking group to the poly (amino acid) carrier.

The Structure of the Immunogens

Usable antibodies can be produced from a variety of benzoyl ecgonine derivatives (U.S. Pat. Nos. 3,917,582; 4,045,420; and 4,197,237). The novel immunogens prepared from the haptens shown in FIG. 2 can produce antibodies that are useful in a benzoyl ecgonine and/or substituted benzoyl ecgonine assay according to the invention when combined with the appropriate tracer.

Figure 6:
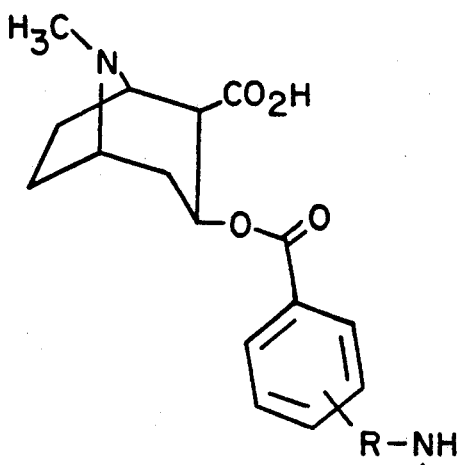
FIG. 6 shows a general structural formula for the immunogens of the present invention.
Figure 8:
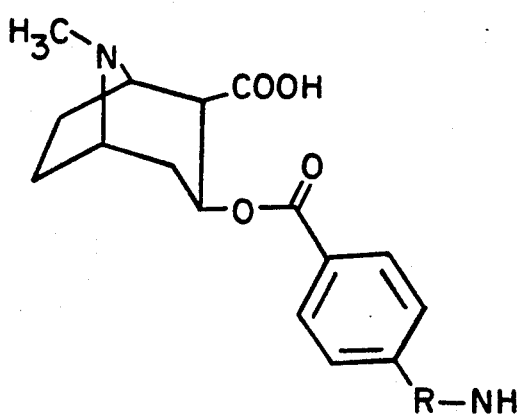
FIG. 8 shows a structural formula for preferred immunogens of the present invention.

The immunogens of the present invention have the general structural formula shown in FIG. 6, and in the preferred form of the invention, the immunogens have the structural formula shown in FIG. 8. This structure is preferred because the best recognition of the common moiety of cocaine and cocaine metabolites, the azabicyclooctane ring system, occurs when the benzoyl group is substituted at a position as distance as possible from the ring system. Although glutaraldehyde derivatized bovine serum albumin is the poly(amino acid) in this preferred form, it should be understood that various protein carriers maybe employed, including albumins, serum proteins, e.g., globulins, ocular lens proteins, lipoproteins and the like. Illustrative protein carriers include bovine serum albumin, keyhold limpet hemocyanin, egg ovalbumin, bovine gamma-globulin, thyroxine binding globulin, etc. Alternatively, synthetic poly(amino acid) may be prepared having a sufficient number of available amino groups such as lysines. The Corresponding glutaraldehyde derivatives of the above poly(amino acid) carriers may also be employed.

The immunogens can be prepared by coupling a compound of the class shown in FIG. 2 with a poly(amino acid) or a derivative of a poly(amino acid), as will be discussed in the context of the synthetic method and the Examples below.

The Structure of the Tracers

Figure 7:
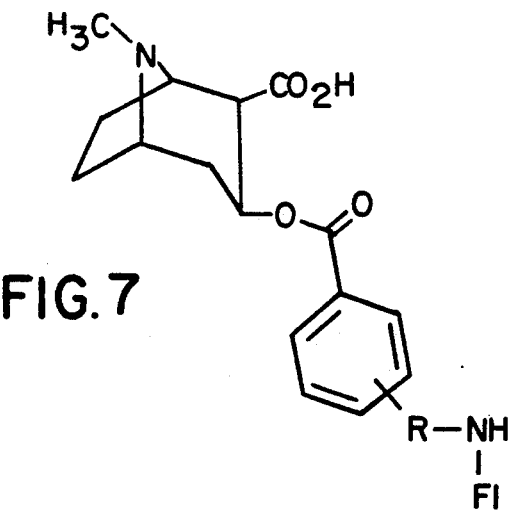
FIG. 7 shows a general structural formula for the tracers of the present invention.

The possible variations in the structure of the tracers of the invention are even greater than the possible variations in the structure of the haptens thereof. The tracers of the present invention have the general structural formula shown in FIG. 7, wherein Fl represents a fluorescein moiety or a fluorescein derivative. In a preferred form of the invention, the tracers have the structural formula shown in FIG. 9.

The tracer is a benzoyl ecgonine derivative that is linked to a fluorescein derivative by, for example, an amido, amidino, triazinylamino, carbamino or thiocarbamido group, as shown in FIG. 11. The tracers are prepared by linking the appropriate fluorescein derivative to a benzoyl ecgonine derivative containing an amino, carboxylic acid, imidate, hydrazide, isocyanate, thioisocyanate, or the like group, as will be discussed in the context of the synthetic method and the Examples below.

By way of example, any of the following fluorescein derivatives can be used:

| | |
|---|---|
| Fl—NH$_2$ | fluorescein amine |
| Fl—NHCOCH$_2$I | α-iodoacetamidofluorescein |

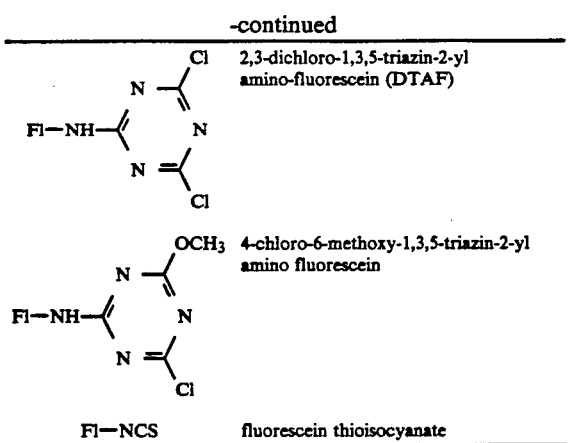

| | |
|---|---|
| Fl—NH-[triazine with 2 Cl] | 2,3-dichloro-1,3,5-triazin-2-yl amino-fluorescein (DTAF) |
| Fl—NH-[triazine with OCH3 and Cl] | 4-chloro-6-methoxy-1,3,5-triazin-2-yl amino fluorescein |
| Fl—NCS | fluorescein thioisocyanate |

The Antibodies

The antibodies of the present invention are prepared by developing a response in animals to the immunogens described above. The immunogen is administered to animals such as rabbits or sheep by a series of injections, in a manner well-known to those skilled in the art.

Synthetic Methods

Both the immunogens and the tracers of the present invention can be made from a precursor having the general structural formula shown in FIG. 10, where X is $NH_2$ when he preparation is directed to an immunogen, and $NH_2$, COOH or CN when the preparation is directed to a tracer;

R is a linking group including up to 2 heteroatoms when the preparation is directed at an immunogen, and R is a linking group including up to 4 heteroatoms when the preparation is directed at a tracer, and a total of from 1 to 8 carbon atoms and heteroatoms; and $Z_1$, $Z_2$, $Z_3$, and $Z_4$ are each independently H or F when the preparation is directed to a tracer, and are each H when the preparation is directed to an immunogen.

The Synthesis of the Immunogens

The immunogens of the present invention are made by coupling a hapten, such as that shown by the general structure of FIG. 2, to a poly(amino acid). The poly(amino acid) moiety can be linked to the hapten by an amide, a urea or a thiourea linkage. Other linkages, such as amidine and azimido, have been employed in U.S. Pat. Nos. 3,917,582; 4,045,420; and 4,197,237. In a preferred embodiment, the poly(amino acid) is bovine serum albumin glutaraldehyde derivative (BSAG) and the hapten is shown in FIG. 14. The hapten is preferably coupled by simply mixing the hapten and BSAG in an aqueous buffer near neutral pH. This avoids any self-condensation of the hapten during the coupling process than can occur during the standard activation methods.

The novel glutaraldehyde carrier proteins are prepared from glutaraldehyde and the desired poly(amino acid). The most convenient source of glutaraldehyde is the 25% aqueous glutaraldehyde available from Sigma Chemical Company, St. Louis, Mo. This glutaraldehyde solution must be pretreated with decolorizing charcoal to remove polymeric glutaraldehyde. The pretreatment is a mixing process that lasts of 1 to 15 minutes, but preferably about 5 minutes and is followed by removal of the charcoal particles with a small particle filter, preferably 0.2 to 0.45 u filters, available from Millipore Corporation, Bedford, Mass.

The pretreated glutaraldehyde is added to an aqueous solution of the poly(amino acid). It is important to note that when high concentrations of the poly(amino acid) solution are used, polymerization takes place and the resulting derivatized poly(amino acid) is not useful as a carrier protein. The preferred glutaraldehyde derivatized carrier has minimal cross-linking between protein molecules. This improves the handling of the carrier, for example, ease of purification, ease of reaction, ease or immunogen purification and ease of molar substitution ratio determination. It is also important to note that the mixing of the pretreated glutaraldehyde and the poly(amino acid) must be immediate and gentle to avoid polymerization.

The glutaraldehyde derivatized poly(amino acid) is particularly advantageous for coupling to amino acid compounds. The tendency of amino acids to self condense under normal coupling reaction conditions, such as by activation of the poly(amino acid) carboxylic acid groups with EDC, DCC, or the like, can be avoided. However, any primary or secondary amine can be easily coupled to this carrier protein.

The immunogens are prepared by coupling the glutaraldehyde derivatized poly(amino acid) with a hapten that contains a reactive amino group, such as in FIG. 2. This is accomplished by simply mixing the two materials in an aqueous buffered solution near neutral pH. Immunogens may also be prepared from these haptens by activation of the poly(amino acid) carboxylic acid groups with EDC, DCC or the like, by procedures known to anyone skilled in the art. The hapten may also be converted to an isocyanate or isothiocyanate by reaction with phosgene or thiophosgene, respectively, and these may be coupled to a poly(amino acid). The haptens which require protection of the carboxylic acid group, such as tert-butyl ester, benzyl ester, or the like, prior to reaction with phosgene or thiophosgene and then removal of the protecting group after coupling to the poly(amino acid).

The synthesis of the above haptens (immunogen precursors) are accomplished in very similar ways. FIG. 2 shows an immunogen precursor class in accordance with a preferred embodiment of the method of the present invention.

In general, the hapten is prepared by reaction of ecgonine methyl ester with the appropriate benzoyl chloride derivative, such as chloromethylbenzoyl chloride, cyanobenzoyl chloride, or the like, to produce the corresponding cocaine derivative. The hydrolysis of the methyl ester of the cocaine derivative produces the corresponding benzoyl ecgonine derivative. The various benzoyl chloride derivatives are available for purchase or can be prepared by known procedures by anyone skilled in the art.

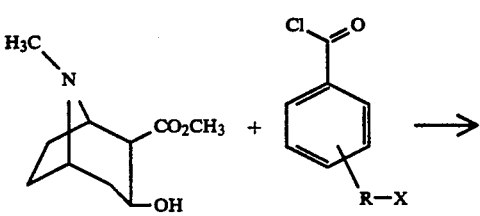

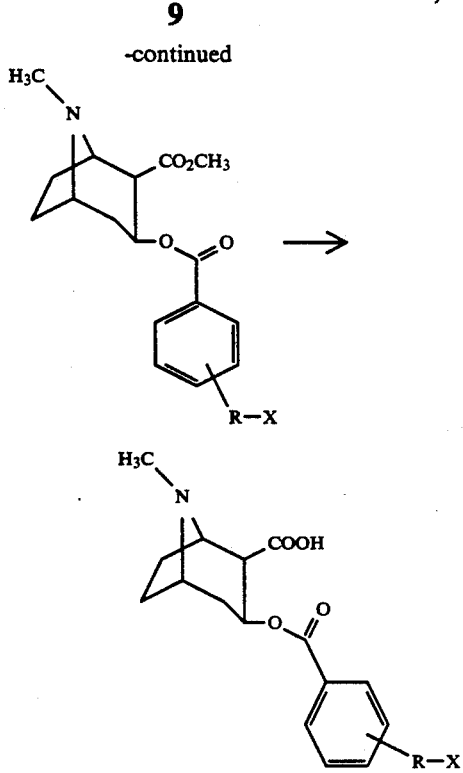

In the presently preferred embodiment, the preferred hapten is a 4-(aminomethyl)benzoyl ecgonine which is prepared from ecgonine methyl ester and 4-(chloromethyl)benzoyl chloride. The structure is shown in FIG. 14.

In the case where X is a halogen (Cl, Br or I), it is best to convert the X group into another group prior to hydrolysis of the methyl ester. The conversion of X into an amino group is accomplished by reaction with ammonium hydroxide. Hydrolysis of the methyl ester leads to benzoyl ecgonine haptens where $X=NH_2$. The conversion of X into a cyano group can be accomplished by reaction with cyanide ion. Hydrolysis of the methyl ester can produce the corresponding cyano benzoyl acgonine derivatives. These are then converted into imidate haptens (U.S. Pat. No. 4,123,431).

Suitable cocaine haptens corresponding to the above benzoyl ecgonine haptens can be obtained by avoiding the methyl ester hydrolysis step.

The Synthesis of the Tracers

Figure 12:
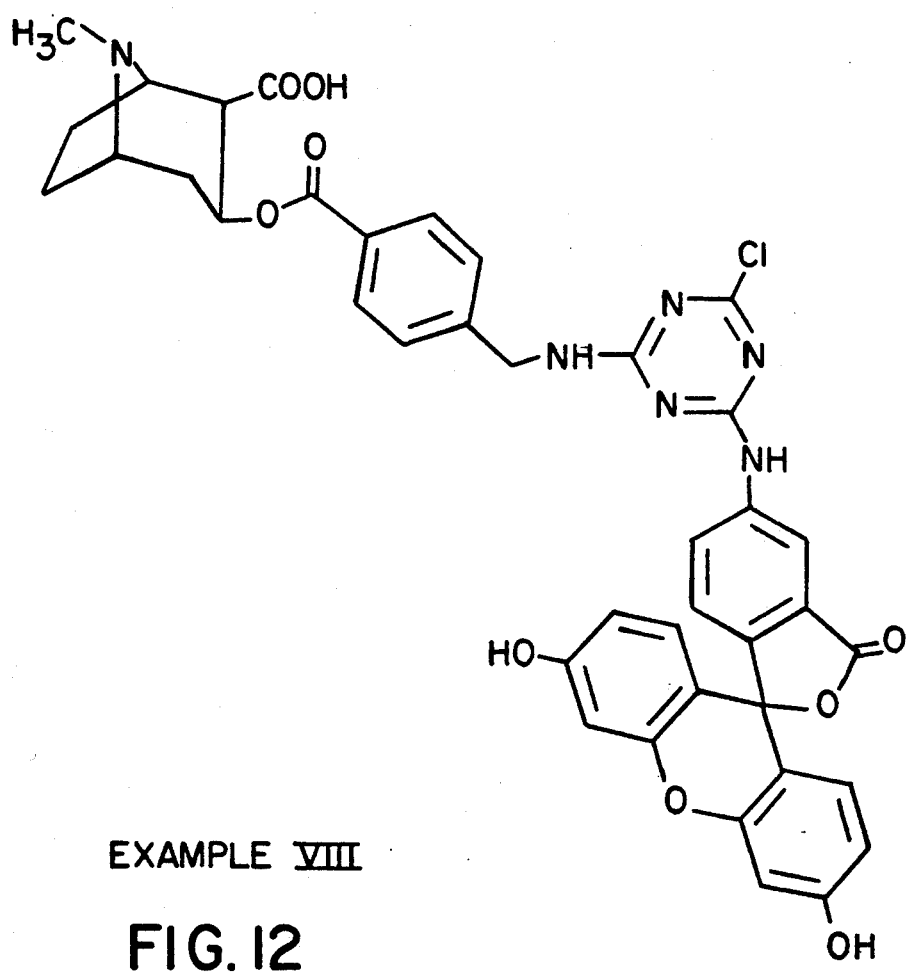

The tracers of the present invention are made by coupling a fluorescein moiety, or a derivative of fluorescein other than carboxyfluorescein, to the general structure shown in FIG. 10 when X is $NH_2$, COOH, or CNOR. The fluorescein moiety can be linked to the amino, carboxyl, or imidate functional group by a carbonylamino, an amidine, a urea, a thiourea or triazinylamino linkage, as shown in FIG. 11. In the presently preferred embodiment the fluorescein derivative is 5-(4,6-dichloro-1,3,5-triazin-2-yl) amino)-fluorescein which is coupled to 4-(aminomethyl)benzoyl ecgonine to form the preferred tracer. The structure is shown in FIG. 12.

All benzoyl ecgonine derivatives that have a terminal amino group, such as amino, hydrazinyl, hydrazido or the like, are coupled to fluorescein isothiocyanate, DTAF or alkoxy DTAF by simply mixing the two materials in solution. The amino group can be converted to the isocyanate and thioisocyanate groups by reaction with phosgene and thiophosgene, respectively. These are then condensed with aminofluorescein to produce the tracer.

All benzoyl ecgonine derivatives that have a terminal nitrile group are converted to imidates in anhydrous alcohol in the presence of hydrogen chloride gas. The imidate is then coupled to fluorescein amine to prepare the tracer.

All benzoyl ecgonine derivatives that have a terminal carboxylic acid group, such as carboxylic acid, (aminohydroxy)alkylcarboxylic acid or the like, are coupled to aminofluorescein by the active ester method.

The preparation of the amino benzoyl ecgonine derivatives was described in the immunogen preparation section and in U.S. Pat. No. 3,888,866. The nitrile benzoyl ecgonine derivatives have been described earlier in U.S. Pat. No. 4,123,431. The carboxylic acid benzoyl ecgonine derivatives can be prepared from the corresponding protected carboxylic acid benzoyl chloride derivatives. The carboxylic acid can be protected as an ester, such as benzyl ester, tert-butyl ester, or the like, which is removed after coupling to ecgonine methyl ester. The protected carboxylic acid benzoyl chloride derivatives can be prepared from known procedures by anyone skilled in the art.

The Assay

The particular tracers and antibodies of the present invention have been found to produce surprisingly good results in fluorescence polarization assays for benzoyl ecgonine and substituted benzoyl ecgonine compounds. FIG. 1 shows the general structure of the benzoyl ecgonine compound that can be quantitatively or qualitatively determined in accordance with the present invention. The assay of the present invention provides a more rapid benzoyl ecgonine and substituted benzoyl ecgonine compounds assay method than most prior art methods, because it requires no specimen treatment before analysis. The assay system accurately measures the presence or quantity of benzoyl ecgonine and substituted benzoyl ecgonine compounds in a sample, because antibody specificity precludes detection of compounds other than benzoyl ecgonine and substituted benzoyl ecgonine compounds.

In accordance with the analytical methods of the present invention, i.e., the methods of determining benzoyl ecgonine and substituted benzoyl ecgonine compounds by a fluorescence immunoassay procedure using the tracer compounds and immunogens of the invention, a sample containing or suspected of containing benzoyl ecgonine or substituted benzoyl ecgonine compounds is intermixed with a biologically acceptable salt of a tracer and an antibody specific to benzoyl ecgonine and substituted benzoyl ecgonine compounds and the tracer. The antibody is produced using the immunogen as described above. The benzoyl ecgonine and substituted benzoyl ecgonine compounds and tracer compete for limited antibody sites, resulting in the formation of complexes. By maintaining constant the concentration of tracer and antibody, the ratio of benzoyl ecgonine and substituted benzoyl ecgonine compounds-antibody complex to tracer-antibody complex that is formed is directly proportional to the amount of benzoyl ecgonine and substituted benzoyl ecgonine compounds in the sample. Therefore, upon exciting the mixture with linearly polarized light and measuring the polarization of the fluorescence emitted by a tracer and a tracer-antibody complex, on is able to quantitatively determine the amount or qualitatively determine the presence of benzoyl ecgonine and substituted benzoyl ecgonine compounds in the sample.

The results can be quantified in terms of net millipolarization units and span (in millipolarization units). The measurement of net millipolarization units indicates the maximum polarization when a maximum amount of the tracer is bound to the antibody, in the absence of any benzoyl ecgonine or substituted benzoyl ecgonine compounds. The higher the net millipolarization units, the better the binding of the tracer to the antibody. The span is an indication of the difference between the net millipolarization and the amount of tracer bound to the antibody at the minimum benzoyl ecgonine concentration above which the sample is defined as containing benzoyl ecgonine and/or substituted benzoyl ecgonine compounds. A larger span provides for a better numerical analysis of data. The preferred antibody-tracer combination has a span of at least 25 millipolarization units, but a span of at least 5 millipolarization units is acceptable. It is important to note that the span varies depending on the sample site used which in turn may alter the preferred combination.

Table I shows the results obtained with various embodiments of the present invention, in terms of span and net millipolarization unit, at a sample size of 10 μl. In all instances, bovine serum albumin glutaraldehyde derivative was used as the protein carrier. As seen from the data in Table I, an assay produced from an immunogen made from the hapten of FIG. 14 used in combination with the tracer of FIG. 12 and a 10 μl sample size provides excellent results. Accordingly, this combination is presently the most preferred form of the invention for a sample size of 10 μl. In addition, the hapten/tracer combinations represented by the combinations of FIGS. 15 and 12, FIGS. 14 and 13, and FIGS. 15 and 13, also produced acceptable results and are alternative preferred combinations.

TABLE I

| Hapten used in Immunogen for Antibody | Tracer | Net Polarization* | Span** |
|---|---|---|---|
| FIG. 14 | FIG. 12 | 188 | 30 |
| FIG. 14 | FIG. 13 | 123 | 20 |
| FIG. 15 | FIG. 12 | 173 | 16 |
| FIG. 15 | FIG. 13 | 114 | 19 |

*In millipolarization units
**In millipolarization units at a benzoyl ecgonine concentration of 0.3 ug/ml and a 10 μl sample size.

The pH at which the method of the present invention is practiced must be sufficient to allow the fluorescein moiety of the tracers to exist in their open form. The pH may range from about 3 to 12, more usually in the range of from about 5 to 10, most preferably from about 6 to 9. Various buffers may be used to achieve and maintain the pH during the assay procedure. Representative buffers include borate, phosphate, carbonate, tris, barbital and the like. The particular buffer employed is not critical to the present invention, but the tris and phosphate buffers are preferred. The cation portion of the buffer will generally determine the cation portion of the tracer salt in solution.

Riboflavin binding protein (RBP) is added to the sample or to one or more of the assay reagents in order to bind any riboflavin present in the sample into RBP-riboflavin complexes, thus eliminating potential fluorescence interference. RBP is a protein of approximately 32,000 M.W. which is isolated from egg whites. Upon isolation from the egg, each molecule of RBP contains one molecule of riboflavin. This, the holoprotein form of RBP, must be converted to the apoprotein form by dialysis, under acidic conditions, to remove the bound riboflavin. The RBP apoprotein utilized in the present invention is commercially available from Sigma Chemical Company, St. Louis, Mo. The amount used is not critical, provided a sufficient quantity is used to bind all free riboflavin in the sample.

The preferred method of the improved assay of the present invention will now be discussed in detail. The assay is a "homogeneous assay," which means that the end polarization readings are taken from a solution in which bound tracer is not separated from unbound tracer. This is a distinct advantage over heterogeneous immunoassay procedures such as those where the bound tracer must be separated from the unbound tracer before a reading can be taken.

The reagents for the fluorescence polarization assay of the present invention comprise antibody for benzoyl ecgonine and substituted benzoyl ecgonine compounds and tracer. Additionally, largely conventional solutions, including a pretreatment solution, a dilution buffer, benzoyl ecgonine calibrators and benzoyl ecgonine controls are desirably prepared. Typical solutions of these reagents, some of which are described below, are commercially available in assay "kits" from Abbott Laboratories, Abbott Park, Ill.

All percentages expressed herein are weight-volume unless otherwise indicated. The tracer formulation presently preferred is 82 nanomolar tracer in: 0.1 molar tris buffer at pH 7.65; 10% cholic acid; 0.1% sodium azide; and 0.01% bovine gamma-globulin. The antiserum formulation comprises rabbit serum diluted with: 0.1 molar sodium phosphate buffer at pH 7.5; 0.1% sodium azide; 0.01% bovine gamma-globulin; and 2% ethylene glycol (volume/volume).The pretreatment solution comprises: 0.1 molar tris buffer at pH 7.5; 0.1% sodium azide; 3 mg/ml riboflavin binding protein; 0.01% bovine gamma-globulin. The dilution buffer comprises: 0.1M sodium phosphate buffer at pH 7.5; 0.1% sodium azide; and 0.01% bovine gamma-globulin. Benzoyl ecgonine controls comprising benzoyl ecgonine in normal human urine are provided at concentrations of 0.5 and 3.0 micrograms per milliliter with 0.1% sodium azide as a preservative are also useful.

The preferred procedure is especially designed to be used in conjunction with the Abbott Tdx ® Analyzer available from Abbott Laboratories, Irving, Tex. Fifty microliters of urine is required. The calibrators, controls, or unknown samples are pipetted directly into the sample well of the TDx sample cartridge. One of the advantages of this procedure is that the sample does not require any special preparation. The assay procedure from this point is fully automated.

If a manual assay is being performed, then the sample is mixed with the pretreatment solution in dilution buffer and a background reading is taken. The tracer is then mixed with the assay. The antibody is then finally mixed into the test solution. After incubation, a fluorescence polarization reading is taken.

The fluorescence polarization value of each calibrator, control or sample is determined and is printed on the output tape of an instrument such as the Abbott TDx ® Analyzer. A standard curve is generated in the instrument by plotting the polarization of each calibrator versus its concentration using a nonlinear regression analysis. The concentration of each control of sample is read off the stored calibration curve and printed on the output tape.

With respect to the foregoing preferred procedure, it should be noted that the tracer, antibody, treatment solution, calibrators and controls should be stored between about 1° and about 8° C. while the dilution buffer should be stored at ambient temperature. A standard curve and controls should be run every two weeks, with each calibrator and control run in duplicate. All samples can be run in duplicate.

It should be understood that the foregoing detailed description and the following Examples are intended to be illustrative, but not limiting, with respect to the scope of the present invention. Various modifications will become apparent to one skilled in the art, and thus it is intended that the scope of the invention be defined solely by the claims and legal equivalents thereof.

EXAMPLES

Examples I through XII describe experiments that were performed in accordance with the concepts of the present invention. Examples I through III are directed to preparation of an immunogen useful for producing antibody; Examples IV through VII and X through XII are directed to the synthesis of procursors for immunogens and tracers; and Examples VIII and IX are directed to the preparation of tracers.

EXAMPLE I

Bovine Serum Albumin Glutaraldehyde Derivative

A 15% aqueous glutaraldehyde solution (Sigma) was mixed with discolorizing charcoal for about 5 minutes and filtered through a 0.1 µl filter (Millipore). A 0.65 ml aliquot of this solution was added to each of 4 bottles containing 13 ml of aqueous bovine serum albumin (3.8 mg/ml) and immediately slowly mixed by rotation for 18 hours. The four solutions were combined and dialysed in a cellulose dialysing tube (SpectraPor, MW 12,000–14,000) against 0.06M carbonate buffer pH 9.5 at room temperature for 18 hours. After removal of the solution from the dialysing tube, the protein concentration was determined to be 3.68 mg/ml by the Biuret protein concentration determining method.

EXAMPLE II 4-(Aminomethyl)benzoyl Ecgonine Immunogen 4-(Aminomethyl)benzoyl ecgonine bis-(trifluoroacetic acid) salt (228 mg) was dissolved in 11.4 mg of 0.01M phosphate buffer containing 0.15M NaCl pH 7.5. A 4 ml aliquot of this solution was added to 25 ml of bovine serum albumin glutaraldehyde derivative (3.68 mg/ml) with stirring and the mixture was stirred at room temperature for 18 hours. The mixture was dialysed in a cellulose dialysing tube (Spectra/Por, MW 12,000–14,000) against 0.1M tris (hydroxymethyl)-aminomethane (Aldrich) containing 0.15M Nacl pH 8.0 at room temperature for 18 hours. The solution from the dialysing tube was purified on a Sephadex column packed and eluted with 0.15M NaCl to yield the purified immunogen.

EXAMPLE III 4-(2-Aminoethyl)benzoyl Ecgonine Immunogen 4-(2-Aminoethyl)benzoyl ecgonine bis (trifluoroacetic acid) salt (42.6 mg) was dissolved in 5 ml of 0.01M phosphate buffer containing 0.15M NaCl pH 7.5. A 3.5 ml aliquot of this solution was added to 10.8 ml of bovine serum albumin glutaraldehyde derivative (3.65 mg/ml) with stirring and the mixture was stirred at room temperature for 18 hours. The mixture was dialysed in a cellulose dialysing tube (Spectra/Por MW 12,000–14,000) against 0.1M tris (hydroxymethyl)-aminomethane (Aldrich) containing 0.15M NaCl pH 8.0 at room temperature for 18 hours. The solution from the dialysing tube was purified on a Sephadex column packed and eluted with 0.15M NaCl to yield the purified immunogen.

EXAMPLE IV

Ecgonine Methyl Ester

Cocaine (Merck) (3.91 g) was dissolved in 100 ml 1N HCl and heated to reflux for 19 hours. After cooling to room temperature, the benzoic acid was filtered and washed with water. The water was washed with chloroform several times and the water was removed in vacuo. The residue was dissolved in 200 ml anhydrous methanol and the solution was saturated with HCl gas. The reaction mixture was refluxed for 17 hours. After cooling to room temperature, the solvent was removed in vacuo. The residue was dissolved in water and basified with potassium carbonate to pH 9. The basic water was extracted with methylene chloride several times. After drying the organic layer over sodium sulfate, the solvent was removed in vacuo to yield ecgonine methyl ester as an oil.

EXAMPLE V

4'-(chloromethyl)cocaine

Ecgonine methyl ester (0.42 g) was dissolved in 4 ml dry benzene and 0.6 ml dry triethylamine. 4-(Chloromethyl)benzoyl chloride (Aldrich) (0.86 g) was added and the mixture was stirred at room temperature for 2 days. The solvent was removed in vacuo. The residue was dissolved in methylene chloride and extracted with 1N HCl several times. The acidic water extracts were combined and basified with potassium carbonate to pH 9. The basic water was extracted with methylene chloride several times. The organic layer was removed in vacuo to yield 4'-(chloromethyl)cocaine.

EXAMPLE VI

4'-(Aminomethyl)cocaine

4'-(Chloromethyl)cocaine (0.6 g) was dissolved in 25 ml p-dioxane and 25 ml concentrated ammonium hydroxide. The solution was stirred at room temperature for 18 hours. The solvent was removed in vacuo to yield the 4'-(aminomethyl)cocaine.

EXAMPLE VII

4'(Aminomethyl)benzoyl Ecgonine

4'-(Aminomethyl)cocaine (0.3 g) was dissolved in 15 ml p-dioxane and 15 ml distilled water. The solution was refluxed for 66 hours. After cooling to room temperature, the solvent was removed in vacuo. The residue was dissolved in 4 ml p-dioxane and 4 ml distilled water and di-tert-butyldicarbonate (Aldrich) (0.3 g) was added. The mixture was stirred at room temperature for 3 hours. The solvent was removed in vacuo. The 4′-((t-butoxycarbonylamino)methyl)-benzoyl ecgonine was obtained pure by chromatography on silica gel eluted with the appropriate mixture of chloroform and methanol. The purified product was dissolved in 5 ml methylene chloride and 5 ml trifluoroacetic acid and stirred for 2 hours at room temperature. The solvent was removed in vacuo to yield the pure 4-(aminomethyl)benzoyl ecgonine bis(trifluoroacetic acid) salt.

EXAMPLE VIII (N-(4-Chloro-6-(5-fluoresceinylamino)-1,3,5-triazin--2-ylamino)methyl) benzoyl ecgonine 4-(Aminomethyl)benzoyl ecgonine bis (trifluoroacetic acid) salt (17.4 mg) and 5-(4,6-dichloro-1,3,5-triazin-2-yl-amino) fluorescein (24 mg) were dissolved in 2 ml methanol and 0.1 ml triethylamine. The reaction was stirred for 16 hours at room temperature and the solvent was removed in vacuo. The tracer was purified on silica gel plates eluted with the appropriate mixture of chloroform and methanol.

EXAMPLE IX (N-(4-chloro-6-(6-fluoresceinylamino)-1,3,5-triazin--2-ylamino)methyl) benzoylecgonine The same procedure is used as in Example VIII except that 6-(4,6-dichloro-1,3,5-triazin-2-yl-amino)-fluorescein is used in place of 5-(4,6-dichloro-1,3,5-triazin-2-yl-amino)fluorescein.

EXAMPLE X

4′-(2-Bromoethyl)cocaine.

4-(2-Bromoethyl)benzoic acid (Pfaltz and Bauer) (0.55 g) was suspended in 20 ml dry benzene and 0.6 ml thionyl chloride was added. The mixture was heated to reflux under $N_2$ for 5 hours and the solvent was removed in vacuo. The residue was dissolved in 7 ml dry benzene; the solution was added to ecgonine methyl ester 0.14 g) and 0.2 ml triethylamine was added. After stirring for 5 days at room temperature, the reaction was diluted with 50 ml methylene chloride and extracted with 50 ml in CHl. The acid layer was basified with potassium carbonate to pH 9 and extracted with methylene chloride several times. The methylene chloride was dried over sodium sulfate and removed in vacuo to yield 4′-(2-bromoethyl)cocaine.

EXAMPLE XI

4′-(2-Aminoethyl)cocaine

4′-(2-Bromoethyl)cocaine (0.16 g) was dissolved in 10 ml p-dioxane and 15 ml concentrated ammonium hydroxide and stirred at room temperature for 64 hours. The solvent was removed in vacuo to yield 4′-(2-aminoethyl)cocaine.

EXAMPLE XII 4-(2-Aminoethyl)benzoyl Ecgonine

4′-(2-Aminoethyl)cocaine (0.13 g) was dissolved in 15 ml p-dioxane and 15 ml distilled water and refluxed for 64 hours. The solvent was removed in vacuo. The residue was dissolved in 10 ml p-dioxane and 10 ml distilled water and di-tert-butyldicarbonate (Aldrich) (0.2 g) and 0.2 ml triethylamine were added. The mixture was stirred at room temperature for 2.5 hours. The solvent was removed in vacuo. The residue was chromatographed on silica gel eluted with the appropriate mixture of chloroform and methanol to yield 4′-(2-(6-tert-butoxycarbonylamino)ethyl)benzoyl ecgonine. The purified product (44 mg) was dissolved in 4 ml methylene chloride and 4 ml trifluoroacetic acid. The mixture was stirred at room temperature for 2 hours. The solvent was removed in vacuo to yield 4-(2-aminoethyl)-benzoyl ecgonine bis(trifluoroacetic acid) salt.

We claim:

1. A compound comprising the structure:

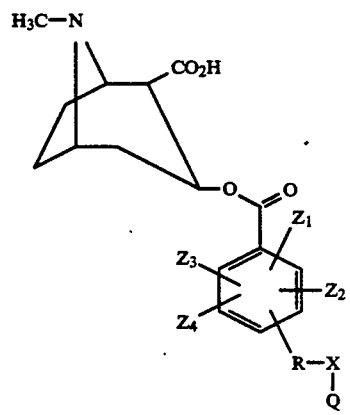

wherein
Q is fluorescein, or a fluorescein derivative other than carboxyfluorescein;
X is NH or CO;
R is a linking group including up to 4 heteroatoms and having a total of from 1 to 8 carbon atoms and heteroatoms; and
$Z_1$, $Z_2$, $Z_3$ and $Z_4$ are each independently H or F.

2. The compound of claim 1 wherein Q is a fluorescein derivative and RX is a member of the group consisting of —CO—NH—, —CNH—NH—, —NH—CO—NH—, —NH—CS—NH—,

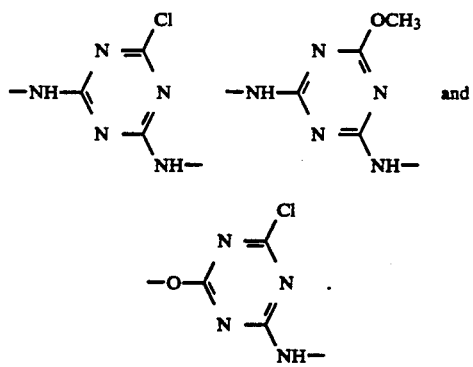

3. The compound of claim 1 wherein XQ is 4-chloro-6-fluorescein-5-ylamino)-1,3,5-triazin-2-yl.

4. The compound of claim 1 wherein XQ is 4-chloro-6-(fluorescein-6-ylamino)-1,3,5-triazin-2-yl.

5. The compound of claim 1 wherein XQ is 4(fluorescein-5-ylamino)-6-methoxyl-1,3,5-triazin-2-yl.

6. The compound of claim 1 where XQ is fluorescein-5-ylamino.

7. The compound of claim 1 where XQ is (fluorescein-6-ylamino)thiocarbonyl.

8. An antibody raised in response to the compound of claim 9 said antibody being reactive with the benzoyl ecgonine portion of said compound.

9. A compound comprising the structure:

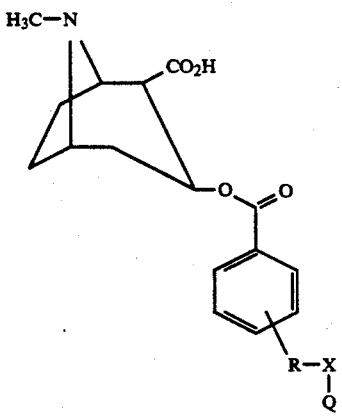

wherein
Q is a poly (amino acid) or a poly (amino acid) derivative;
X is NH; and
R is an alkylene group having a total of from 1 to 8 carbon atoms.

10. The compound of claim 9 wherein R is selected from the group consisting of methylene and ethylene.

11. The compound of claim 9 wherein R is methylene.

12. The compound of claim 9 wherein R is ethylene.

13. The compound of claim 9 wherein Q is glutaraldehyde-derivatized bovine serum albumin.

14. A process for detecting or measuring the concentration of benzoyl ecgonine and substituted benzoyl ecgonine compounds which comprises the steps of:
(a) contacting a sample with riboflavin binding protein, with a benzoyl ecgonine antiserum and with a compound according to claim 1 capable of producing a detectable fluorescence polarization response to the presence of the benzoyl ecgonine antiserum,
(b) passing plane polarized light through the resulting solution from step (a) to obtain a fluorescence polarization response; and
(c) detecting the fluorescence polarization response of the solution of step (b) as a measure of the presence or the amount of benzoyl ecgonine and substituted benzoyl ecgonine compounds in the sample.

15. The process of claim 14 wherein the benzoyl ecgonine antiserum contains the antibodies of claim 9.

16. The process of claim 14 wherein the tracer is a compound according to any one of claims 1, 2, 3, 4, 5, 6, or 7.

* * * * *

UNITED STATES PATENT AND TRADEMARK OFFICE
CERTIFICATE OF CORRECTION

PATENT NO. : 5,202,270

DATED : April 13, 1993

INVENTOR(S) : F.S. Ungemach, et al.

It is certified that error appears in the above-identified patent and that said Letters Patent is hereby corrected as shown below:

Column 18, line 24, delete "9" and insert --8--

Signed and Sealed this

Fifth Day of July, 1994

*Attest:*

*Attesting Officer*

BRUCE LEHMAN

*Commissioner of Patents and Trademarks*